(12) United States Patent
Yeh et al.

(10) Patent No.: US 11,510,308 B2
(45) Date of Patent: Nov. 22, 2022

(54) NEUTRON BEAM GENERATING DEVICE

(71) Applicant: HERON NEUTRON MEDICAL CORP., Hsinchu County (TW)

(72) Inventors: Jyi-Tyan Yeh, Hsinchu County (TW); Yen-Wan Hsueh Liu, Hsinchu (TW); Zhen-Fan You, Yilan County (TW)

(73) Assignee: HERON NEUTRON MEDICAL CORP., Hsinchu County (TW)

( * ) Notice: Subject to any disclaimer, the term of this patent is extended or adjusted under 35 U.S.C. 154(b) by 329 days.

(21) Appl. No.: 16/865,430

(22) Filed: May 4, 2020

(65) Prior Publication Data

US 2020/0353291 A1     Nov. 12, 2020

(30) Foreign Application Priority Data

May 7, 2019   (TW) .................................. 108115761

(51) Int. Cl.
| | |
|---|---|
| *H05H 3/06* | (2006.01) |
| *A61N 5/10* | (2006.01) |
| *G21K 1/02* | (2006.01) |
| *G21K 5/04* | (2006.01) |

(52) U.S. Cl.
CPC ............. *H05H 3/06* (2013.01); *A61N 5/1078* (2013.01); *G21K 1/02* (2013.01); *G21K 5/04* (2013.01); *A61N 2005/109* (2013.01); *A61N 2005/1095* (2013.01); *A61N 2005/1098* (2013.01)

(58) Field of Classification Search
CPC .......... H05H 3/06; H05H 6/00; A61N 5/1078; A61N 2005/109; A61N 2005/1095; A61N 2005/1098; A61N 5/1081; A61N 2005/1094; A61N 5/1077; A61N 5/10; A61N 2005/1022; A61N 2005/1092; G21K 1/02; G21K 5/04; G21K 5/10
USPC .................................. 250/251, 492.1–492.3
See application file for complete search history.

(56) References Cited

U.S. PATENT DOCUMENTS

| | | | |
|---|---|---|---|
| 3,715,597 A | | 2/1973 | Hofmann et al. |
| 3,796,878 A | * | 3/1974 | Offermann ............... G21K 5/10 378/197 |
| 4,192,998 A | * | 3/1980 | Azam ...................... A61N 5/10 976/DIG. 428 |
| 4,938,916 A | * | 7/1990 | Dance ...................... G21K 5/04 976/DIG. 428 |
| 7,576,344 B2 | | 8/2009 | Ein-Gal |
| 2013/0066135 A1 | | 3/2013 | Rosa et al. |
| 2017/0062086 A1 | * | 3/2017 | Park, Jr. ................... G21G 1/10 |

(Continued)

FOREIGN PATENT DOCUMENTS

| | | |
|---|---|---|
| CN | 1686617 A | 10/2005 |
| CN | 105120954 A | 12/2015 |
| CN | 206026890 U | 3/2017 |

(Continued)

*Primary Examiner* — Michael Maskell
(74) *Attorney, Agent, or Firm* — CKC & Partners Co., LLC

(57) ABSTRACT

A neutron beam generating device includes a supporting base, an outer shell, a target material, and a first pipe. The outer shell surrounds a rotating axis, rotatable engages the supporting base, and has a first opening. The target material is disposed in the outer shell. The first pipe extends from the first opening of the outer shell along the rotating axis to the target material. The first pipe is configured to transmit an ion beam to bombard the target material to generate a neutron beam.

13 Claims, 7 Drawing Sheets

(56) References Cited

U.S. PATENT DOCUMENTS

2019/0105512 A1\*  4/2019  Liu .................... A61N 5/1082
2019/0105513 A1   4/2019  Liu

FOREIGN PATENT DOCUMENTS

| CN | 106605452 A    | 4/2017  |
|----|----------------|---------|
| CN | 206167654 U    | 5/2017  |
| CN | 107789749 A    | 3/2018  |
| CN | 109381802 A    | 2/2019  |
| JP | 2006047115 A   | 2/2006  |
| JP | 2007-240330 A  | 9/2007  |
| JP | 2007-242422 A  | 9/2007  |
| JP | 2007242422 A   | 9/2007  |
| TW | 201034530 A    | 9/2010  |
| TW | I614042 B      | 2/2018  |
| TW | M558633 U      | 4/2018  |
| WO | 2014173741 A1  | 10/2014 |
| WO | 2018/006551 A1 | 1/2018  |

\* cited by examiner

NEUTRON BEAM GENERATING DEVICE

CROSS-REFERENCE TO RELATED APPLICATION

This application claims priority to Taiwan Application Serial Number 108115761, filed May 7, 2019, which is herein incorporated by reference in its entirety.

BACKGROUND

Field of Invention

The present invention relates to a neutron beam generating device.

Description of Related Art

Specifically, the principle of a Boron Neutron Capture Therapy (BNCT) may be as follows: a boron-containing drug is combined with a tumor cell via a blood circulation, and then a neutron beam irradiates around a location of the tumor tissue, so that the boron absorbs neutrons and generates lithium and helium ions to accurately destroy the tumor cells without damaging other normal tissues.

For patients, the BNCT causes minimal damage and does not require surgery and anesthesia. Furthermore, in the treatment of brain tumors, if the BNCT uses thermal neutrons with low penetration, the patient's cranium needs to be opened additionally. In contrast, if the BNCT uses epithermal-neutrons, it is not necessary to open the patient's skull.

However, most of the neutron beam source generators for the BNCT are derived from nuclear reactor. Because the nuclear reactor cannot usually be installed in a hospital, doctors and patients need to cooperate with the location of the nuclear reactor for treatment. Compared with this, an accelerator-type neutron beam source generator is not only low-cost, but also can be installed in a hospital to save time for the doctors and the patients.

In summary, there is an urgent need to develop the accelerator-type neutron beam source generators to facilitate the development of the BNCT.

SUMMARY

The invention provides a neutron beam generating device.

In some embodiments, a neutron beam generating device includes a supporting base, an outer shell, a target material, and a first pipe. The outer shell surrounds a rotating axis, rotatable engages the supporting base, and has a first opening. The target material is disposed in the outer shell. The first pipe extends from the first opening of the outer shell along the rotating axis to the target material. The first pipe is configured to transmit an ion beam to bombard the target material to generate a neutron beam.

In some embodiments, the rotating axis passes through the target material.

In some embodiments, the first pipe is spaced apart from the supporting base by a distance.

In some embodiments, the outer shell has a passage arranged along a first direction with the target material and configured for the neutron beam to pass through and leave the outer shell, and the first direction intersects the rotating axis.

In some embodiments, the first direction is substantially perpendicular to the rotating axis.

In some embodiments, the neutron beam generating device further includes a reflector located in the outer shell and on a side of the target material away from the passage.

In some embodiments, the neutron beam generating device further includes a neutron moderation structure located in the outer shell and between the target material and the passage and spaced apart from an extension line of a central axis of the first pipe.

In some embodiments, the neutron beam generating device further includes a second pipe and a rotating joint connected between and communicating the first and second pipes and configured so that the first and second pipes are relatively rotated based on the rotation axis.

In some embodiments, the neutron beam generating device further includes an accelerator connected to an end of the second pipe opposite to the first pipe and configured to generate the ion beam to enter the second pipe.

In some embodiments, the supporting base has a second opening, and the outer shell passes through the second opening.

In some embodiments, the neutron beam generating device further includes a first joint structure located at an outer surface of the outer shell, wherein the supporting base includes a second joint structure located at an inner edge of the second opening, and the first joint structure slidably engages the second joint structure.

In some embodiments, the second joint structure is a recess portion of the supporting base, and the first joint structure is a limiting protrusion and configured to rotate relative to the recess portion.

In some embodiments, the recess portion has a joint surface that has a centerline of a curvature and a radius of the curvature, the centerline of a curvature substantially coincides with the rotating axis, and the radius of curvature is a distance between the joint surface and the rotating axis.

In some embodiments, the outer shell includes a bearing protruding from the supporting base along the rotating axis and supported by the supporting base, and the first pipe passes through the bearing.

In the aforementioned configurations, an ion beam generated by the accelerator disclosed in the present disclosure passes through the first pipe and enters the outer shell along the central axis extension line of the first pipe, so there is no need to change the moving direction of the ion beam. At the same time, the outer shell rotates uniaxially with the first pipe as an axis, so that the channel of the outer shell changes position with the rotation. Therefore, when the outer shell rotates relative to the supporting base based on a rotating axis, the emission direction of the neutron beam will change according to the position of the channel. Therefore, for a patient in a fixed posture state, the neutron beam generating device can irradiate an affected portion of the patient at an appropriate angle, thereby improving the accuracy and efficiency of boron neutron capture therapy. According to this, the neutron beam generating device disclosed in the present disclosure can also be called a "variable direction neutron source."

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1A:
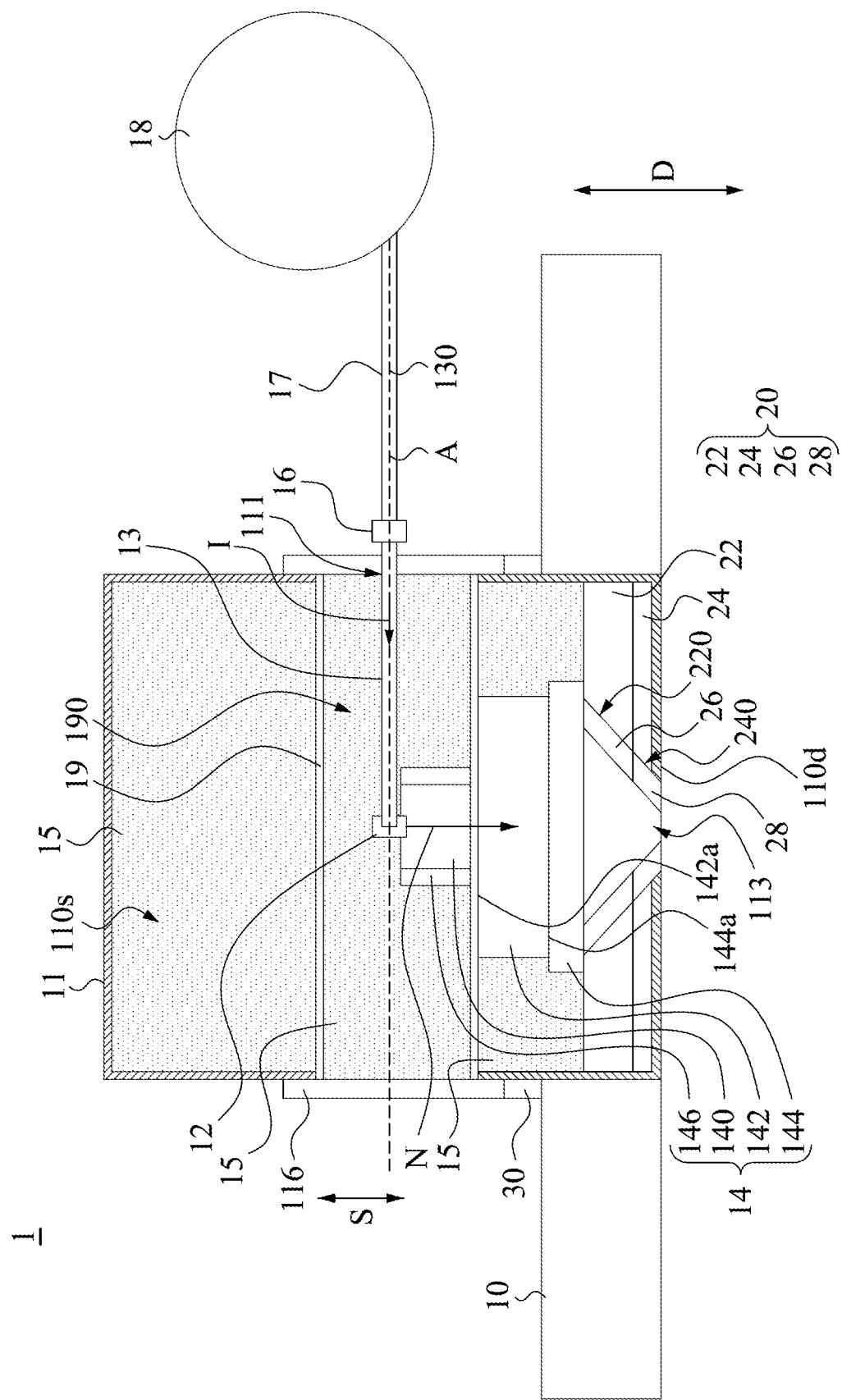
FIGS. 1A, 1B, and 1C respectively illustrate a cross sectional view, a perspective view, and a side view of a neutron beam generating device in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Figure 1B:
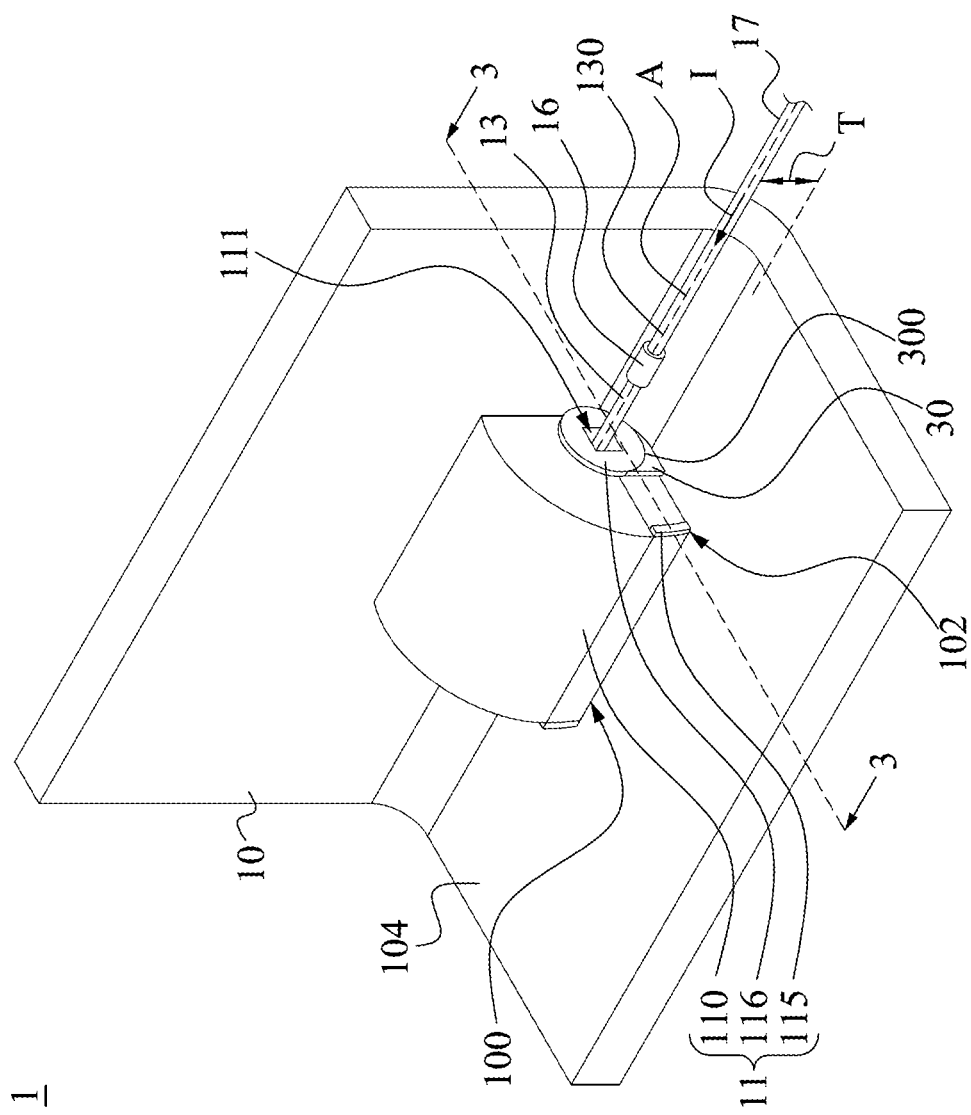
Figure 1C:
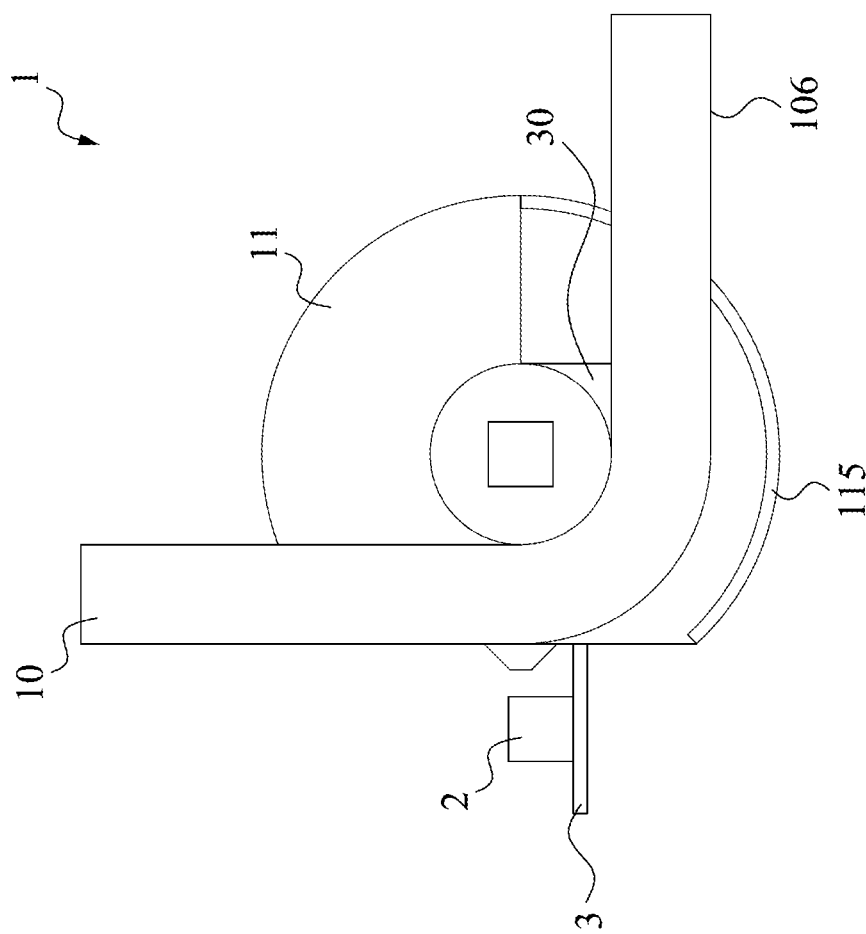

Reference is made to FIGS. 1A, 1B, and 1C. FIGS. 1A, 1B, and 1C respectively illustrate a cross sectional view, a perspective view, and a side view of a neutron beam generating device 1 in accordance with some embodiments of the present disclosure. It is noted that FIGS. 1B and 1C are omitted to show a rotating joint 16, a second pipe 17, and an accelerator 18 for a better understanding of the disclosed embodiment. In the embodiment, the neutron beam generating device 1 includes a supporting base 10, supporting element 30 (See FIG. 1B), an outer shell 11, a first pipe 13 (See FIG. 1A), the rotating joint 16, the second pipe 17, and the accelerator 18, and further includes a target material 12, a neutron moderation structure 14, a reflector 15, an inner shell 19, and a convergence assembly 20 disposed in the outer shell 11. The structure, function, and connection relationship of each element included in the neutron beam generating device 1 will be described in detail below.

Figure 3:
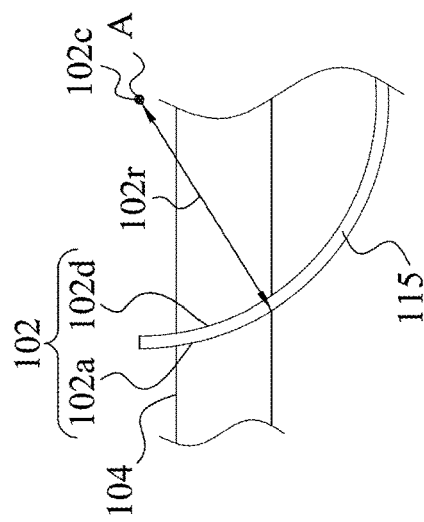
FIG. 3 is a cross sectional view along line 3-3 in FIG. 1B.
Figure 2:
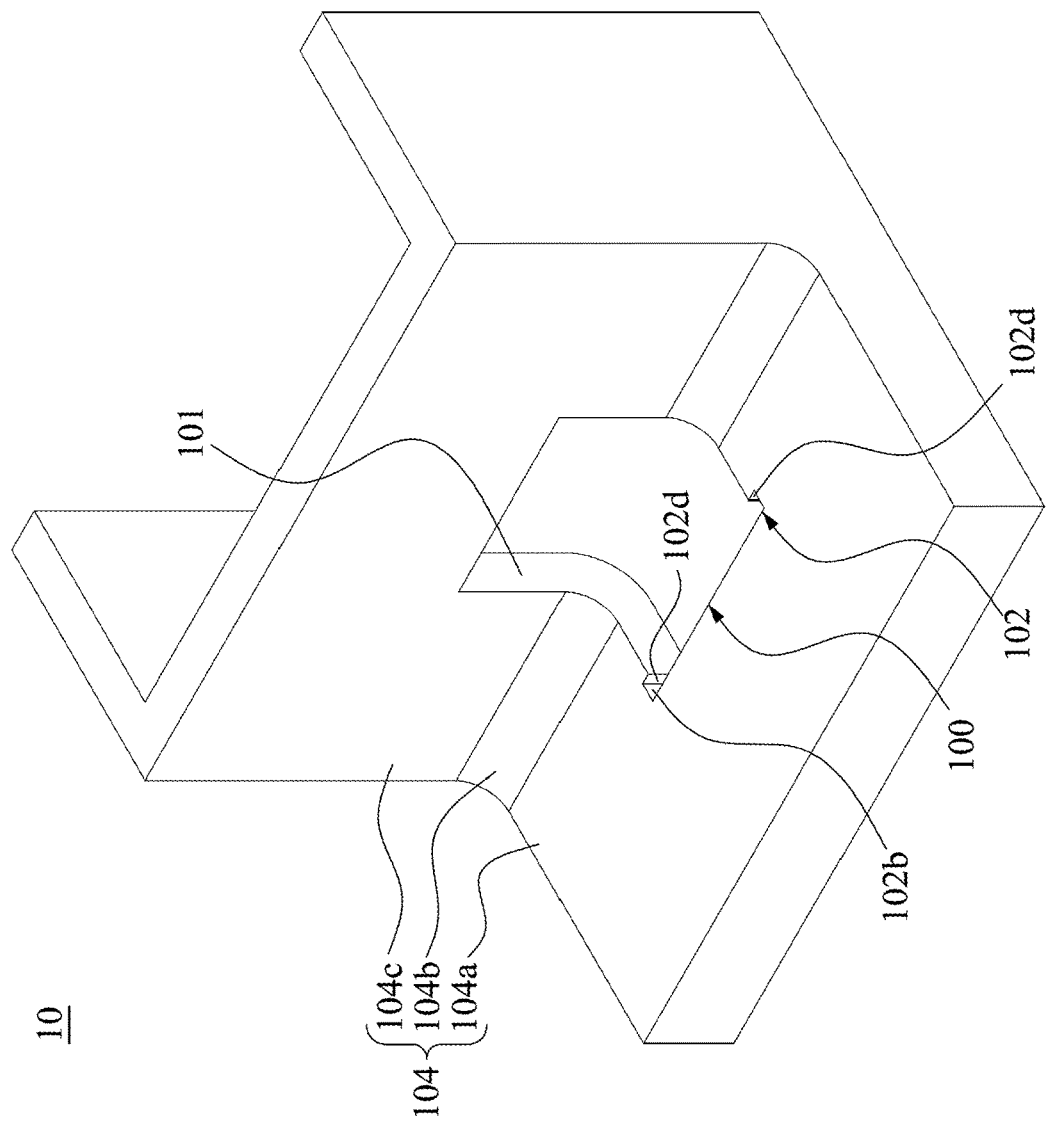
FIG. 2 illustrates a perspective view of a supporting base in accordance with some embodiments of the present disclosure.

Reference is made to FIGS. 2 and 3. FIG. 2 illustrates a perspective view of a supporting base 10 in accordance with some embodiments of the present disclosure. FIG. 3 is a cross sectional view along line 3-3 in FIG. 1B. As shown in FIG. 2, the supporting base 10 is a substantially L-shaped support structure. Specifically, the supporting base 10 has a first curved surface 104 and a second curved surface 106 opposite to the first curved surface 104 (See FIG. 1C), an opening 100 connecting the first and second curved surfaces 104 and 106, and a first joint structure 102.

In FIG. 2, the first curved surface 104 of the supporting base 10 has a first region 104a, a bending region 104b, and a second region 104c which are sequentially connected. An extension surface of the first region 104a intersects an extension surface of the second region 104c. In the embodiment, the extension surface of the first region 104a is substantially perpendicular to the extension surface of the second region 104c, but the present disclosure is not limited thereto. The bending region 104b is connected between the first and second regions 104a and 104c and recesses toward the second curved surface 106 of the supporting base 10 (See FIG. 1C).

In the embodiment, the opening 100 of the supporting base 10 is opened at least in the bending area 104b and extends from the bending region 104b to the first region 104a and the second area 104c on both sides thereof. The first joint structure 102 of the supporting base 10 is located on an inner edge 101 of the opening 100. In the embodiment, the first joint structure 102 of the supporting base 10 is a recess portion and located in the first region 104a, but the present disclosure is not limited thereto. In some embodiments, as long as the structure that can be connected with a second joint structure 115 on the outer shell 11 can be applied to this disclosure as the first joint structure 102. As shown in FIG. 2, the first joint structure 102 recesses from the inner edge 101 of the opening 100 and is defined by a first joint surface 102a (See FIG. 3), a second joint surface 102b (See FIG. 2), and a third joint surface 102d. The first joint surface 102a of the joint structure 102 (See FIG. 3) faces toward the bending region 104b and has a curvature center line 102c and a curvature radius 102r. The second joint surface 102b of the first joint structure 102 faces toward the opening 100 and connected between the first and third joint surfaces 102a and 102d. In FIG. 3, the third joint surface 102d of the first joint structure 102 faces away from the bending region 104b.

Reference is made to FIG. 1B. The outer shell 11 includes a shell body 110 and the second joint structure 115. The shell body 110 of the outer shell 11 passes through the opening 100 of the supporting base 10. The outer shell 11 engages the supporting base 10 at least by the second joint structure 115 and rotates relative to the supporting base 10 based on a rotating axis A.

Reference is made to FIG. 3. In some embodiments, in the supporting base 10, the curvature center line 102c of the first joint surface 102a of the first joint structure 102 coincides with the rotating axis A. Therefore, the curvature radius 102r of the first joint surface 102a is substantially equal to a distance between the first joint surface 102a and the rotating axis A.

Figure 4B:
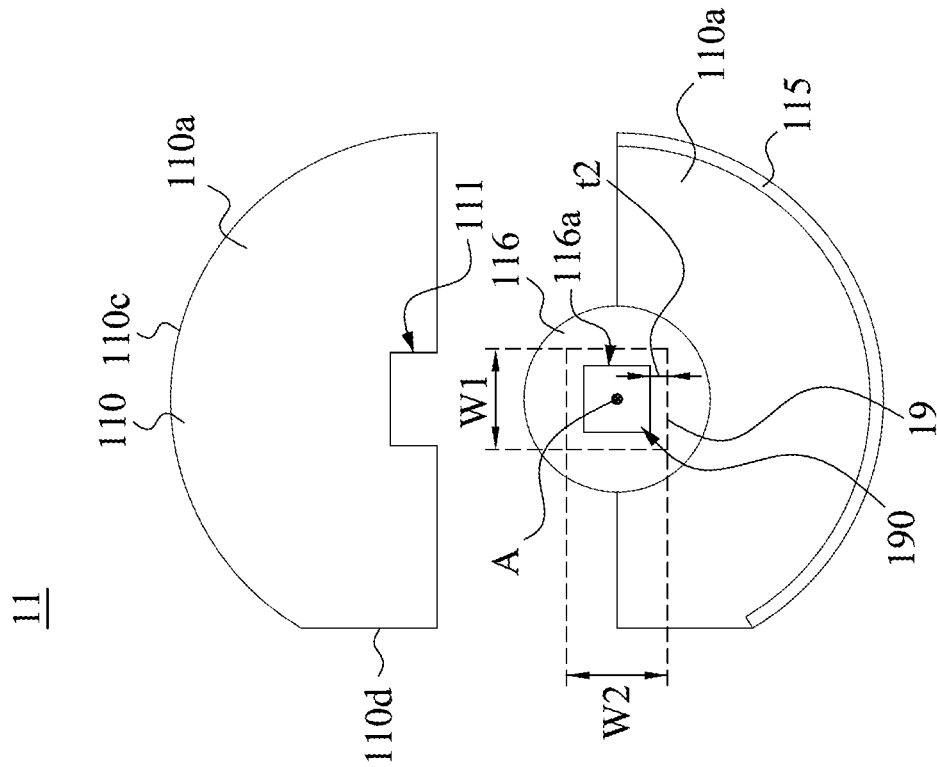
FIG. 4B illustrates an exploded side view of an outer shell in accordance with some embodiments of the present disclosure.
Figure 4A:
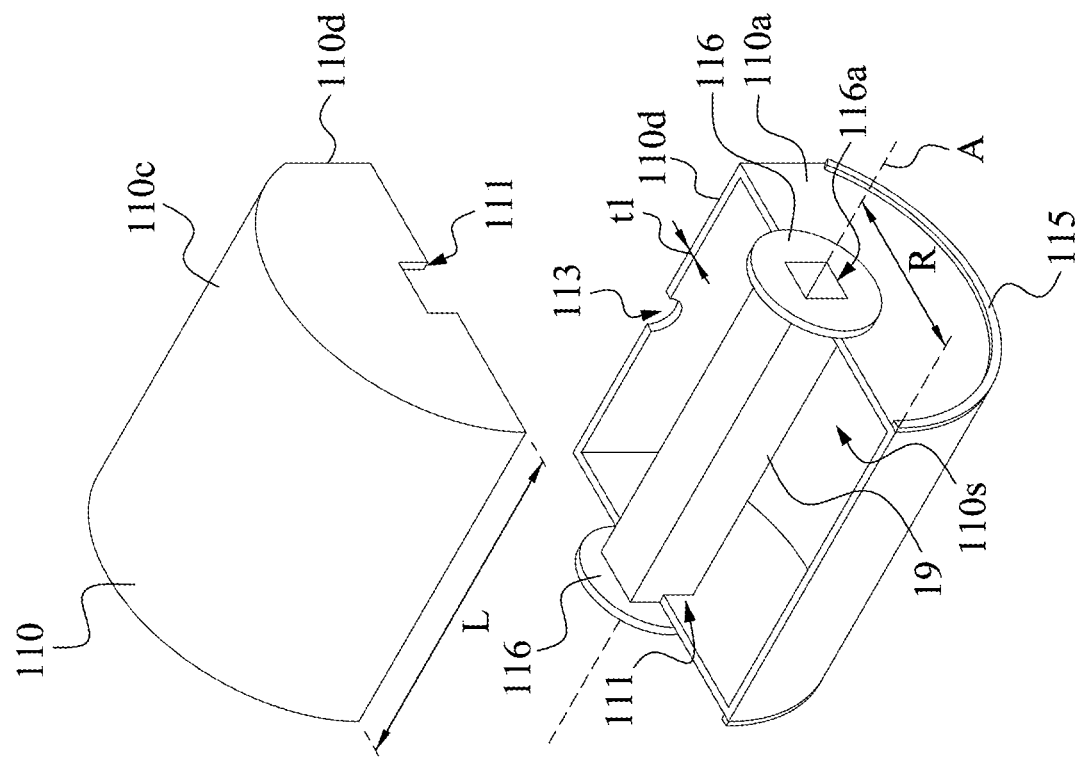
FIG. 4A illustrates an exploded perspective view of an outer shell and an inner shell in accordance with some embodiments of the present disclosure.

Reference is made to FIGS. 4A and 4B. FIG. 4A illustrates an exploded perspective view of the outer shell 11 and the inner shell 19 in accordance with some embodiments of the present disclosure. FIG. 4B illustrates an exploded side view of the outer shell 11 in accordance with some embodiments of the present disclosure. In order to better understand the present disclosure, the outer shell 11 and/or the inner shell 19 of the present disclosure are analyzed in the manner shown in FIGS. 4A and 4B. In the embodiment, the shell body 110 of the outer shell 11 is rotatably engaged with the supporting base 10 around the rotation axis A (See FIG. 1B) and has a thickness t1. In other words, the shell body 110 is formed based on a barrel-shaped structure and a part of the structure is removed along a central axis direction thereof, and thus has a radiation surface 110d.

Specifically, the shell body 110 has an accommodating space 110s, a first outer surface 110a, a second outer surface (not shown) opposite to the first outer surface 110a, a third outer surface 110c connected between the first outer surface 110a and the second outer surface, and the radiation surface 110d. The outer surface 110a and the second outer surface (not shown) are substantially perpendicular to the first curved surface 104 (See FIG. 1B) of the supporting base 10. The third outer surface 110c surrounds the rotating axis A. The radiation surface 110d is substantially flat, but the present disclosure is not limited thereto.

Furthermore, the shell body 110 further has an opening 111 opened therein and a channel 113 (See FIG. 1A and may also refer to as a passage). For example, the opening 111 is opened on the first outer surface 110a of the shell body 110. The channel 113 is opened on the radiation surface 110d of the shell body 110. In FIG. 1A, the channel 113 of the outer shell 11 and the target material 12 disposed in the housing 11 are arranged in a direction D, where the direction D intersects the rotating axis A. In some embodiments, the channel 113 is located in the center of the radiation surface 110d, but the present disclosure is not limited thereto. In the embodiment, the direction D is substantially perpendicular to the rotating axis A. The channel 113 of the outer shell 11 is used for a neutron beam N generated by the target material 12 to pass through and leave the outer shell 11. In FIG. 1B, the opening 111 of the outer shell 11 is used for the first pipe 13 to pass through, so that an ion beam I in the first pipe 13 strikes the target material 12 to generate the neutron beam N.

Reference is made to FIG. 1A. In order to perform a boron neutron capture therapy, the neutron beam N needs to be irradiated with different irradiation positions relative to the affected part of a patient 2 (See FIG. 1C). However, when the patient 2 is undergoing the boron neutron capture treatment, if the posture the patient 2 is changed to match the neutron beam N, the organ of the patient 2 will move during the posture change and affect the effect of the boron neutron capture therapy. Therefore, if the patient 2 is allowed to perform the boron neutron capture therapy while maintaining a fixed posture thereof (for example, lying position), the accuracy and efficiency of the boron neutron capture therapy will be improved.

In order to allow the neutron beam N to illuminate the affected part of the patient 2 in a fixed posture at an appropriate angle, in this embodiment, the ion beam I can first be passed through the first pipe 13 and along a central axis extension line 130 enters the outer shell 11, so there is no need to change a moving direction of the ion beam I. Next, the outer shell rotates uniaxially with the first pipe 13 as an axis, so that the channel 113 of the outer shell 11 changes position as the rotation proceeds. Therefore, when the outer shell 11 is rotated relative to the supporting base 10 based on the rotation axis A, an emission direction of the neutron beam N will change according to the position of the channel 113. According to this, the neutron beam generating device 1 can also be called a "variable direction neutron source."

Alternatively, in some embodiments, the patient 2 can lean against (e.g., lying down) a supporting table 3 (see FIG. 1C). For example, the supporting table 3 is a hospital bed. The supporting table 3 is configured to move relative to the supporting base 10. Therefore, when the emission direction of the neutron beam N is changed, the support table 3 may move relative to the supporting base 10 so that the affected part of the patient 2 can be at an appropriate angle and distance from the outer shell 11. Thereby, the neutron beam N can irradiate the affected part of the patient 2 at an appropriate angle, so as to further improve the accuracy and efficiency of the boron neutron capture therapy. In the embodiment, the neutron beam generating device 1 may be a multi-field irradiation for deep tumor therapy.

Reference is made to FIGS. 4A and 4B. The shell body 110 has a length L in an extending direction of the rotation axis A, and has a maximum distance R between an outer surface of the housing body 110 and the rotation axis A. In some embodiments, the thickness t1 of the shell body 110 may be about 0.01 m, the maximum distance R between the rotating axis A and the shell body 110 may be about 0.86 m, and the length L of the shell body 110 in the extension direction of the rotating axis A may be about 1.4 m, but the present disclosure is not limited thereto.

In FIGS. 4A and 4B, the outer shell 11 further includes a pair of bearings 116 respectively protruding from the first outer surface 110a and the second outer surface (not shown) along the rotating axis A and are away from the shell body 110. In the embodiment, the bearing 116 is a disc-shaped structure, but the present disclosure is not limited thereto. In FIG. 1B, the supporting element 30 is located between the bearing 116 and the supporting base 10. Specifically, the supporting element 30 is fixed to the first curved surface 104 of the supporting base 10, and a top surface 300 thereof conforms to a partial contour of the bearing 116. The support element 30 is used to support the outer shell 11 and a plurality of components provided in the outer shell 11 through the bearing 116, and further assist the outer shell 11 to rotate relative to the support element 30 based on the rotating axis A. Furthermore, the bearing 116 has an opening 116a to communicate the accommodation space 110s (see FIG. 4A) of the shell body 110 to the outside of the outer shell 11.

In some embodiments, the bearing 116 and the supporting element 30 may be provided, and the first joint structure 102 and the second joint structure 115 may be omitted.

Reference is made to FIGS. 1B, 4A, and 4B. In the embodiment, the outer shell 11 further slidably engages the first joint structure 102 of the supporting base 10 by its second joint structure 115 (see FIG. 1B). Specifically, the second joint structure 115 is a limiting protrusion, but the present disclosure is not limited thereto. In the embodiment, the second joint structure 115 is a slide rail structure. A plurality of the second joint structures 115 are disposed on the shell body 110 and protrude from the first outer surface 110a and the second outer surface (not shown) of the shell body 110 along the rotation axis A. Furthermore, the second joint structure 115 further extends along an outer edge of the first outer surface 110a and is at least partially located between the first joint surface 102a (see FIG. 3) and the third joint surface 102d (see FIG. 3) of the joint structure 102 of the supporting base 10. A rotation center line of the second joint structure 115 is the rotating axis A. When the outer shell 11 is rotated relative to the supporting base 10 based on the rotating axis A (see FIG. 1B), the second joint structure 115 is limited to the first joint structure 102 of the supporting base 10 and rotates at least against the first joint surface 102a the first joint structure 102.

In some embodiments, the second joint structure 115 may be a recessed structure, and the first joint structure 102 may be a protruding structure engaging with the second joint structure 115, but the present disclosure is not limited thereto. In some embodiments, any structure that can make the first and second joint structures 102 and 115 engage with each other, and further make the outer shell 11 rotate relative to the support base 10 can be applied to this disclosure.

In FIGS. 4A and 4B, the inner shell 19 is connected between the pair of the bearing 116 and surrounds the rotating axis A. The inner shell 19 has a thickness t2 and has an inner space 190 (FIG. 4B). Furthermore, the inner shell 19 is a square hollow beam, but the present disclosure is not limited thereto. The square hollow beam has a first width W1 and a second width W2. In the embodiment, the opening 116a of the bearing 116 is connected to both ends of the inner shell 19, and further communicates the inner space 190 of the inner shell 19 to the outside of the outer shell 11. The inner shell 19 is used to support and fix the target material 12, the first pipe 13, a part of the neutron moderation structure 14, and a part of the reflector 15 therein to strengthen the structural strength of the neutron beam generating device 1 and can improve convenience when servicing the neutron beam generating device 1. In some embodiments, the first width W1 of the inner shell 19 may be about 0.3 m, and the second width W2 of the inner shell 19 may be about 0.3 m, but the present disclosure is not limited thereto.

In FIG. 1A, the target material 12 is located in the accommodating space 110s of the outer shell 11 and further in the inner space 190 of the inner shell 19. Furthermore, the target material 12 is located at an end of the first pipe 13 and is adjacent to the neutron moderation structure 14. In the embodiment, the rotating axis A extends through the target material 12. The impacted surface (not shown) of the target material 12 is substantially perpendicular to the central axis extension line 130 of the first pipe 13. In the embodiment, the target material 12 includes beryllium (Be), but the present disclosure is not limited thereto.

In FIG. 1A, the first pipe 13 surrounds the rotating axis A, extends from the opening 111 of the outer shell 11 to the target material 12 along the rotating axis A, and is located at least partially in the inner space 190 of the inner shell 19. The first pipe 13 is configured to rotate with the outer shell 11 and a plurality of elements provided in the outer shell 11 relative to the supporting base 10 based on the rotating axis A. Furthermore, the first pipe 13 is configured for the ion beam I generated by the accelerator 18 to pass therethrough, so that the ion beam I may strike the target material 12 to generate the neutron beam N. In the embodiment, the first pipe 13 and the supporting base 10 are separated by a distance T without contact (see FIG. 1B). The central axis extension line 130 of the first pipe 13 passes through the target material 12.

In FIG. 1A, the neutron moderation structure 14 is located between the outer shell 11 and the channel 113 and is spaced apart from the central axis extension line 130 of the first pipe 13. The neutron moderation structure 14 includes a first moderation layer 140, a second moderation layer 142, a third moderation layer 144, and a coating layer 146. However, the neutron moderation structure 14 is not limited to the aforementioned layered stack structure. In some embodiments, any structure that can adjust energy spectrum of the neutron can be applied to the neutron moderation structure 14 disclosed in the present disclosure. In the embodiment, the first, second, and third moderation layers are sequentially stacked along a stacking direction S. As a result, the neutrons produced by the impact of the ion beam I on the target material 12 may pass through the first moderation layer 140, the inner shell 19, the second moderation layer 142, and the third moderation layer 144 in sequence. The neutron adjusts its energy spectrum by the neutron moderation structure 14 as the neutron beam N used in boron neutron capture therapy.

Furthermore, the first moderation layer 140 and the coating layer 146 are located in the inner space 190 of the inner shell 19. The second moderation layer 142 and the third moderation layer 144 of the neutron moderation structure 14 are located in the accommodation space 110s of the shell body 110 and outside the inner space 190 of the inner shell 19. In other words, the first moderation layer 140 is spaced apart from the second moderation layer 142. The coating layer 146 of the neutron moderation structure 14 wraps around the first moderation layer 140.

In some embodiments, the stacking direction S of the neutron moderation structure 14 intersects the central axis extension line 130 of the first pipe 13. In the embodiment, the stacking direction S of the neutron moderation structure 14 is substantially perpendicular to the central axis extension line 130 of the first pipe 13, but the present disclosure is not limited thereto.

In the embodiment, the second moderation layer 142 and the third moderation layer 144 respectively have a first surface 142a and a second surface 144a each facing toward the target material 12. A projected area of the first moderation layer 140 on the first surface 142a along the stacking direction S is smaller than an area of the first surface 142a. A projected area of the second moderation layer 142 on the second surface 144a along the stacking direction S is smaller than an area of the first surface 144a. Under the foregoing structural configuration, the neutron moderation structure 14 an effect of increasing an intensity of an epithermal-neutron flux.

In some embodiments, the first moderation layer 140 of the neutron moderation structure 14 includes iron (Fe). Specifically, an inelastic collision between the iron and the neutrons in the first moderation layer 140 can reduce the speed of the neutron movement.

In some embodiments, the second moderation layer 142 of the neutron moderation structure 14 includes aluminum fluoride, aluminum, lithium fluoride, or combinations thereof, but the present disclosure is not limited thereto. In some embodiments, the third moderation layer 144 of the neutron moderation structure 14 includes lithium fluoride, magnesium fluoride, or combinations thereof, but the present disclosure is not limited thereto. In the embodiment, the coating layer 146 has a material substantially the same as the second moderation layer 142, but the present disclosure is not limited thereto.

In FIG. 1A, the convergence assembly 20 is located between the neutron moderation structure 14 and the channel 113 of the outer shell 11. The convergence assembly 20 includes a first shielding structure 22, a second shielding structure 24, a third shielding structure 26, and a convergence structure 28. The convergence assembly 20 is used to concentrate and maintain the intensity of the epithermal-neutron flux, and at the same time, it can reduce a dose rate of a fast neutron. Further, the first shielding structure 22 has an opening 220. The second shielding structure 24 has an opening 240. The third shielding structure 26 is located on a sidewall of the opening 220 of the first shielding structure 22. The convergence structure 28 is located on a sidewall of the opening 224 of the second shielding structure 24.

In some embodiments, the first shielding structure 22 includes polyethylene mixed lithium carbonate, the second shielding structure 24 includes Teflon, the convergence structure 28 includes bismuth (Bi), and/or the third shielding structure 26 includes polyethylene mixed lithium carbonate. In some embodiments, the third shielding structure 26 includes concentrated lithium ($^6$Li). However, materials of the first shielding structure 22, the second shielding structure 24, the third shielding structure 26, and the convergence structure 28 are not limited to the foregoing materials. Since the above design can enhance the intensity of the epithermal-neutron flux, the energy or current of the proton beam generated by the accelerator 18 can be reduced.

In FIG. 1A, the reflector 15 is disposed on a side of the inner shell 19 opposite to the channel 113, in the inner space 190 of the inner shell 19, and wraps the target material 12. Further, the reflector 15 is disposed on a side of the inner shell 19 in the vicinity of the channel 113 and wraps the neutron moderation structure 14 and convergence assembly 20. The reflector 15 is used to reflect the neutrons far from the channel 113 to increase the epithermal-neutron flux. In practical applications, the neutron beam N generated by the ion beam I impacting the target material 12 is reflected by the reflector 15 that is at a side of the target material 12 opposite to the neutron moderation structure 14, and then the neutron beam N further passes through the neutron moderation structure 14. In some embodiments, the reflector 15 includes lead (Pb), but the present disclosure is not limited thereto.

In FIG. 1A, the rotating joint 16 is connected between and communicates the first and second pipes 13 and 17 and is configured to make the first pipe 13 rotates relative to the second pipe 17 based on the rotating axis A. The second pipe is connected between the rotating joint 16 and the accelerator 18 and extends along the rotating axis A. In the embodiment, the outer shell 11, a plurality of elements provided in the outer shell 11, and the first pipe 13 are rotated relative to the supporting base 10, the rotating joint 16, the second pipe 17, and the accelerator 18 based on the rotating axis A.

In FIG. 1A, the accelerator 18 is connected to an end of the second pipe 17 opposite to the first pipe 13 and is configured to generate the ion beam I to enter the second pipe 17. In the embodiment, the ion beam I is a proton beam, but the present disclosure is not limited thereto. In some embodiments, the energy of the ion beam I is in a range from about 15 MeV to about 35 MeV. In some embodiments, the current of the ion beam I is in a range about 0.2 mA to about 2 mA. Thereby, the ion beam I hits the target material 12 to generate the fast neutron. After the fast neutron passes through the neutron moderation structure 14 and the convergence assembly 20, an adjusted epithermal-neutron beam is generated.

According to the recommendation of the International Atomic Energy Agency (IAEA), the epithermal-neutron flux used for boron neutron capture therapy needs to be greater than or equal to about $10^9$ n·cm$^{-2}$·s$^{-1}$, and the fast neutron dose rate and a gamma ray dose rate are less than about $2\times10^{-11}$ cGy·cm$^2$/n per unit of the epithermal-neutron flux. If the epithermal-neutron flux is too low, it may prolong a treatment time of the patient 2 (see FIG. 1C). If the fast neutron dose rate is too high, it may damage other normal tissues of the patient 2. If the proton energy provided by the accelerator 18 is too high, it may increase the design difficulty of the neutron moderation structure 14, and the yield of neutrons will be limited. If the proton energy provided by the accelerator 18 is too low, the neutron yield is insufficient, and the current needs to be increased to compensate.

In some embodiments, the accelerator 18 is a cyclotron. In some embodiments, the accelerator 18 may be a cyclotron manufactured by Advanced Cyclotron Systems Inc., but the present disclosure is not limited thereto.

Reference is made to FIGS. 5A, 5B, 5C, and 5D. FIGS. 5A, 5B, 5C, and 5D respectively illustrate side views the neutron beam generating device 1 in different operations in accordance with some embodiments.

Figure 5A:
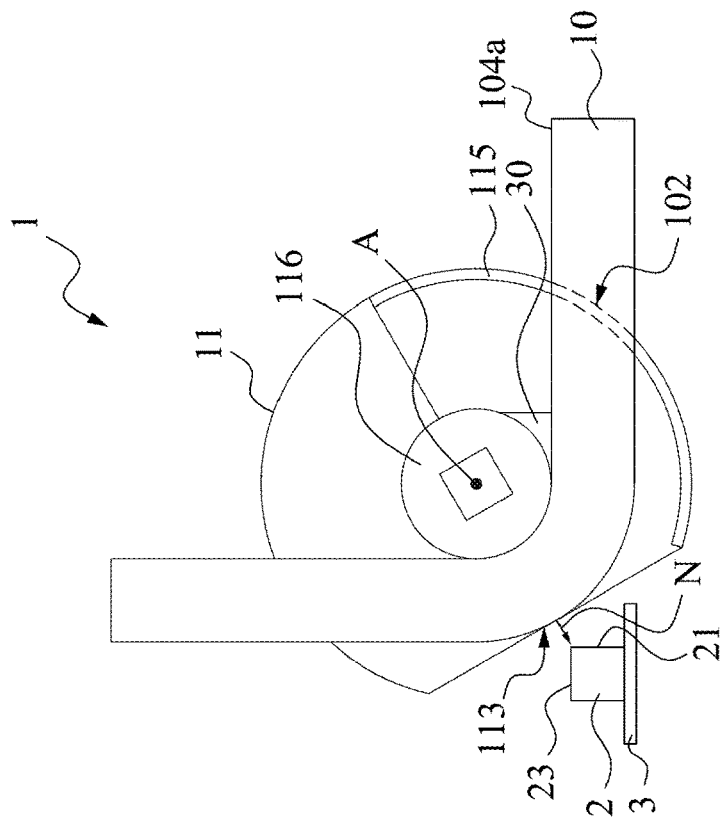
FIGS. 5A, 5B, 5C, and 5D respectively illustrate side views a neutron beam generating device in different operations in accordance with some embodiments, in which compared to FIG. 5A, an out shell in FIG. 5B is rotated about 30 degrees relative to the support base based on the rotation axis, an out shell in FIG. 5C is rotated about 60 degrees relative to the support base based on the rotation axis, and an out shell in FIG. 5D is rotated about 90 degrees relative to the support base based on the rotation axis.

In FIG. 5A, the patient 2 leans against the supporting table 3. At this time, the outer shell 11 of the neutron beam generating device 1 is supported on the supporting base 10 through its bearing 116 and further through the support element 30. Therefore, for the patient 2 in a fixed posture, the neutron beam generating device 1 irradiates an affected part of the patient 2 with the neutron beam N at an appropriate angle through the outer shell 11 thereof. As shown in FIG. 5A, the supporting table 3 is located on the left side of the neutron beam generating device 1. The neutron beam generating device 1 can irradiate a portion 21 of the patient 2.

Figure 5B:
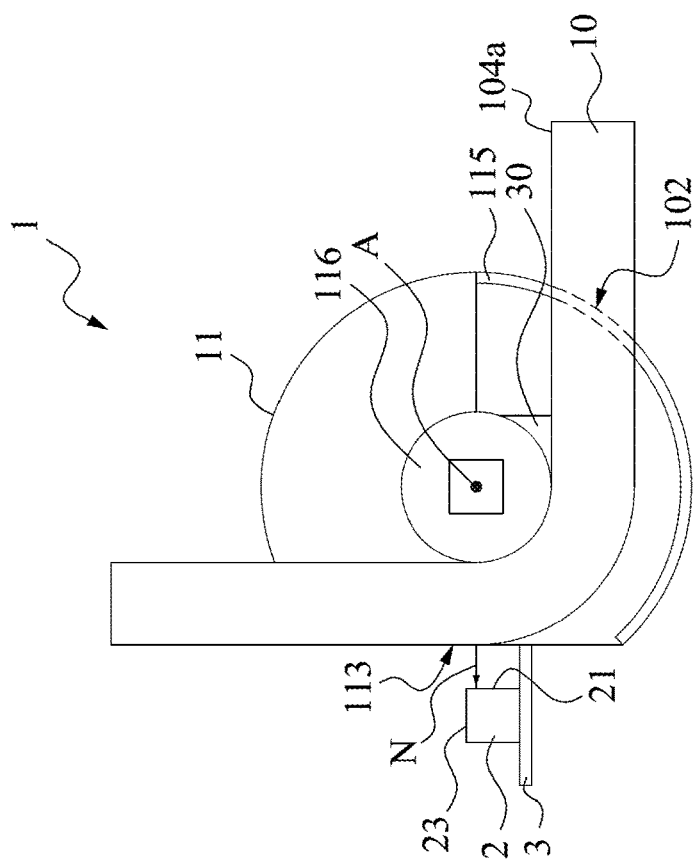

In FIG. 5B, relative to FIG. 5A, the outer shell 11 is rotated about 30 degrees relative to the supporting base 10 based on the rotating axis A. In the embodiment, the rotation of the outer shell 11 is to use a gear transmission method to rotate. Specifically, an outer edge of the second joint structure 115 has a gear structure (not shown). For example, the second joint structure 115 has a curved rack, but the present disclosure is not limited thereto. The neutron beam generating device 1 further includes a power unit (not shown, e.g., motor and gear) disposed on the supporting base 10. In some embodiments, the power unit is disposed on the first curved surface 104 of the supporting base 10 (See FIG. 1B). The power unit provides power so that another gear structure (not shown) snaps onto the gear structure on the second joint structure 115. The power relies on the meshing of gear structures to transmit torque, which in turn transmits power to the outer shell 11. Furthermore, the gear structure on the second joint structure 115 can also be rotated by rotating with other tooth-shaped mechanical parts (such as racks or worms). However, the manner of rotation of the outer shell 11 is not limited to the manner of the gear transmission. For example, the rotation method of the gear transmission may also be a friction transmission method or any suitable mechanical transmission method.

In the embodiment, the second joint structure 115 is limited to the first joint structure 102 of the supporting base 10, and rotates against the first joint surface 102a of the first joint structure 102 (see FIG. 3). Therefore, the outer shell 11 of the neutron beam generating device 1 is supported by the supporting base 10 through its bearing 116, and is rotated relative to the supporting base 10 based on the rotating axis A. In the embodiment, with the rotation of the neutron beam generating device 1, the supporting table 3 moves to the lower left of the neutron beam generating device 1 as shown in FIG. 5B. At this time, the neutron beam generating device 1 can irradiate the portion 21 and a portion of the patient 2.

Figure 5D:
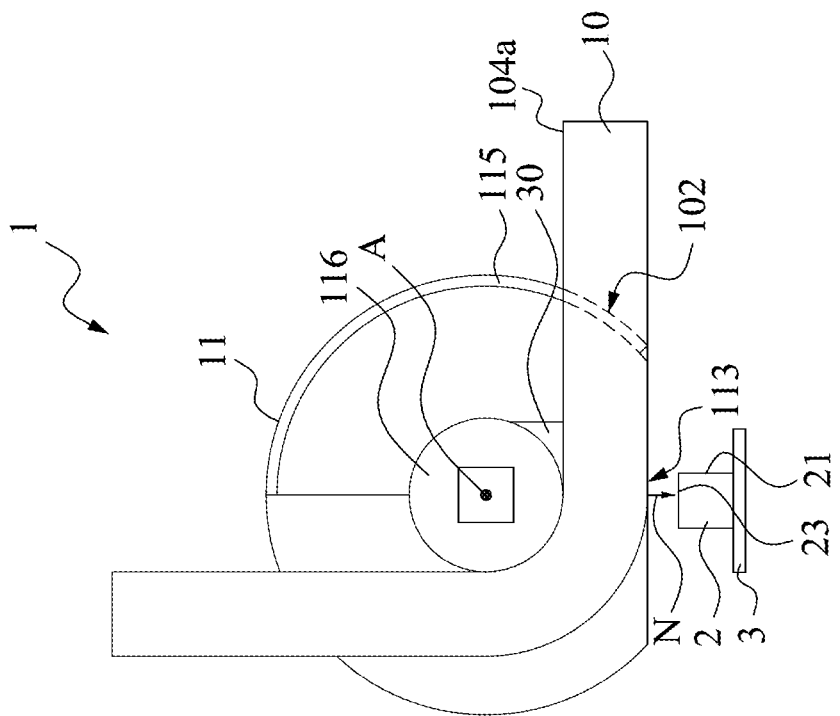
Figure 5C:
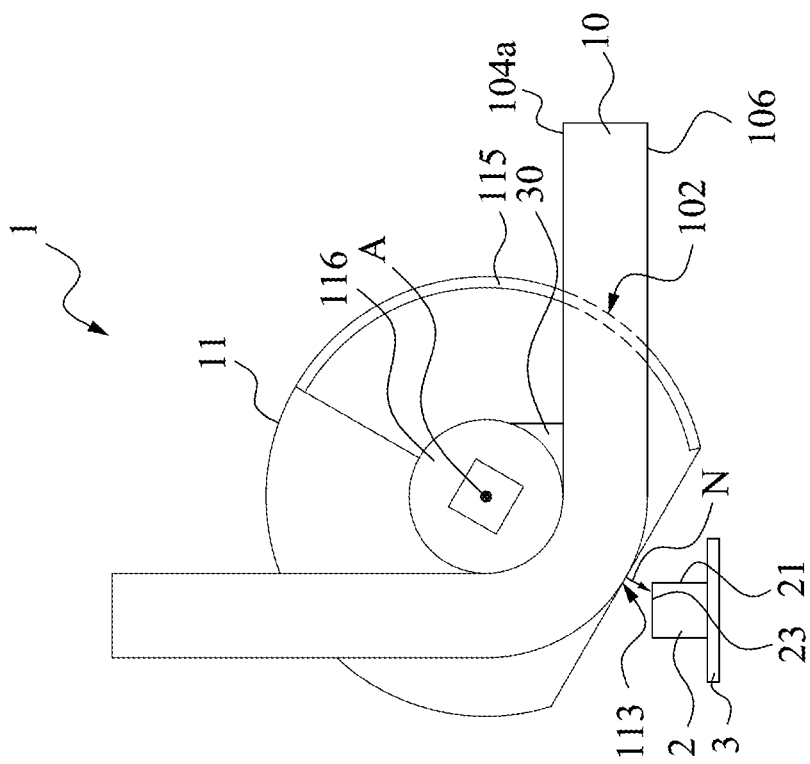

In FIG. 5C, relative to FIG. 5A, the outer shell 11 is rotated about 60 degrees relative to the supporting base 10 based on the rotating axis A. At this time, as the neutron beam generating device 1 rotates, the supporting table 3 moves further down and approaches the neutron beam generating device 1 as shown in FIG. 5C.

In FIG. 5D, relative to FIG. 5A, the outer shell 11 is rotated about 90 degrees relative to the supporting base 10 based on the rotating axis A. At this time, as the neutron beam generating device 1 rotates, the supporting table 3 moves below the neutron beam generating device 1 as shown in FIG. 5D, and then the neutron beam generating device 1 can irradiate the portion 23 of the patient 2.

According to the foregoing embodiments of the disclosure, it can be seen that, an ion beam generated by the accelerator disclosed in the present disclosure passes through the first pipe and enters the outer shell along the central axis extension line of the first pipe, so there is no need to change the moving direction of the ion beam. At the same time, the outer shell rotates uniaxially with the first pipe as an axis, so that the channel of the outer shell changes position with the rotation. Therefore, when the outer shell rotates relative to the supporting base based on a rotating axis, the emission direction of the neutron beam will change according to the position of the channel. Therefore, for a patient in a fixed posture state, the neutron beam generating device can irradiate an affected portion of the patient at an appropriate angle, thereby improving the accuracy and efficiency of boron neutron capture therapy. According to this, the neutron beam generating device disclosed in the present disclosure can also be called a "variable direction neutron source."

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A neutron beam generating device, comprising:
   a supporting base;
   an outer shell surrounding a rotating axis and rotatable engaging the supporting base, wherein the outer shell passes through an opening of the supporting base, and the opening of the supporting base encloses an entirety of the outer shell;
   a target material disposed in the outer shell; and
   a first pipe extending from an opening of the outer shell along the rotating axis to the target material and being configured to transmit an ion beam to bombard the target material to generate a neutron beam.

2. The neutron beam generating device of claim 1, wherein the rotating axis passes through the target material.

3. The neutron beam generating device of claim 1, wherein the first pipe is spaced apart from the supporting base by a distance.

4. The neutron beam generating device of claim 1, wherein the outer shell has a passage arranged along a first direction with the target material and configured for the neutron beam to pass through and leave the outer shell, and the first direction intersects the rotating axis.

5. The neutron beam generating device of claim 4, wherein the first direction is substantially perpendicular to the rotating axis.

6. The neutron beam generating device of claim 4, further comprising a reflector located in the outer shell and on a side of the target material away from the passage.

7. The neutron beam generating device of claim 4, further comprising a neutron moderation structure located in the outer shell and between the target material and the passage and spaced apart from an extension line of a central axis of the first pipe.

8. The neutron beam generating device of claim 1, further comprising a second pipe and a rotating joint connected between and communicating the first and second pipes and configured so that the first and second pipes are relatively rotated based on the rotation axis.

9. The neutron beam generating device of claim 8, further comprising an accelerator connected to an end of the second pipe opposite to the first pipe and configured to generate the ion beam to enter the second pipe.

10. The neutron beam generating device of claim 1, further comprising a first joint structure located at an outer surface of the outer shell, wherein the supporting base comprises a second joint structure located at an inner edge of the opening of the supporting base, and the first joint structure slidably engages the second joint structure.

11. The neutron beam generating device of claim 10, wherein the second joint structure is a recess portion of the supporting base, and the first joint structure is a limiting protrusion and configured to rotate relative to the recess portion.

12. The neutron beam generating device of claim 11, wherein the recess portion has a joint surface that has a centerline of a curvature and a radius of the curvature, the centerline of the curvature substantially coincides with the rotating axis, and the radius of the curvature is substantially a distance between the joint surface and the rotating axis.

13. The neutron beam generating device of claim 1, wherein the outer shell comprises a bearing protruding from the supporting base along the rotating axis and supported by the supporting base, and the first pipe passes through the bearing.

* * * * *